(12) United States Patent
Jung

(10) Patent No.: US 7,690,245 B2
(45) Date of Patent: Apr. 6, 2010

(54) DEVICE FOR TESTING AT LEAST ONE QUALITY PARAMETER OF A FLUID

(75) Inventor: Frank Jung, Neunkirchen (DE)

(73) Assignee: Hydac Filtertechnik GmbH, Sulzbach/Saar (DE)

( * ) Notice: Subject to any disclaimer, the term of this patent is extended or adjusted under 35 U.S.C. 154(b) by 789 days.

(21) Appl. No.: 10/587,305

(22) PCT Filed: Dec. 27, 2004

(86) PCT No.: PCT/EP2004/014725

§ 371 (c)(1),
(2), (4) Date: Jul. 26, 2006

(87) PCT Pub. No.: WO2005/073690

PCT Pub. Date: Aug. 11, 2005

(65) Prior Publication Data

US 2007/0157743 A1    Jul. 12, 2007

(30) Foreign Application Priority Data

Jan. 29, 2004    (DE) .................. 10 2004 004 342

(51) Int. Cl.
*G01N 11/00* (2006.01)
(52) U.S. Cl. ..................................... 73/53.01
(58) Field of Classification Search .................. 73/53.01
See application file for complete search history.

(56) References Cited

U.S. PATENT DOCUMENTS

| | | | |
|---|---|---|---|
| 4,527,436 A | 7/1985 | Jones | |
| 4,976,137 A * | 12/1990 | Decker et al. | 324/439 |
| 5,172,586 A * | 12/1992 | Reed | 73/64.45 |
| 5,717,131 A * | 2/1998 | Sunde et al. | 73/64.41 |
| 5,736,654 A | 4/1998 | Dubois | |
| 7,017,392 B2 * | 3/2006 | Meischner et al. | 73/53.01 |
| 2006/0169033 A1 * | 8/2006 | Discenzo | 73/64.56 |

FOREIGN PATENT DOCUMENTS

| | | |
|---|---|---|
| DE | 24 41 844 | 3/1976 |
| DE | 30 24 823 | 1/1981 |
| DE | 294 569 | 10/1991 |
| DE | 196 27 587 | 1/1998 |
| DE | 100 59 217 | 6/2002 |
| EP | 0 405 475 | 1/1991 |
| FR | 2 792 071 | 10/2000 |
| WO | WO 98/01750 | 1/1998 |

* cited by examiner

*Primary Examiner*—Hezron Williams
*Assistant Examiner*—Rodney T Frank
(74) *Attorney, Agent, or Firm*—Roylance, Abrams, Berdo & Goodman, L.L.P.

(57) ABSTRACT

A device tests at least one quality parameter of a fluid in fluid apparatuses, e.g., working cylinders (10), hydraulic accumulators, valves, filter housings, pressure tubes, which at least temporarily accommodate a given fluid volume in at least one fluid chamber (12, 14). The fluid volume is stored in a storage unit (16) with the aid of a control mechanism (16) after being discharged from the fluid apparatus in order to be redirected from there into a measuring element (22, 24) to verify the respective quality parameter of the fluid. The inventive device makes it possible to specifically obtain a statement about the operability of the respective fluid apparatus within a very short period of time.

33 Claims, 1 Drawing Sheet

DEVICE FOR TESTING AT LEAST ONE QUALITY PARAMETER OF A FLUID

FIELD OF THE INVENTION

The present invention relates to a device for testing at least one quality parameter of a fluid in fluid devices such as working cylinders, hydraulic accumulators, valves, filter housings, flexible pressure tubing, etc.

BACKGROUND OF THE INVENTION

Subsequently published DE 102 47 353 discloses a process for reducing the flow dependence of measuring instruments for determination of impurities as indication of the quality of a fluid, especially solid impurities such as particles in fluids. A particle count sensor operates in particular on the basis of the light blocking principle, and is mounted in a measuring cell of the measuring device. The measuring device has a specifiable input cross-section for the flow of fluid. The sensor generates a light beam cross-sectional area over which the flow of fluid is conducted for detection of an impurity. Particle count sensors operating on the light blocking principle determine the relative proportion of the light beam cross-sectional area (perpendicular to the optical axis) covered by projection of a pollutant particle in this plane.

DE 198 60 169 A1 discloses a process for qualitative determination of small amounts of water in multicomponent systems in the liquid state of aggregation, oil in particular. The process is characterized by repetition of the following process steps several times:
  incomplete extraction of moisture from the multicomponent system by a carrier gas;
  quantitative determination of the amount of moisture extracted by measurement of the relative humidity in the carrier gas, the carrier gas volume, and the temperature; and
  conversion to the amount of moisture of the multicomponent system after determination of the mass of the multicomponent system and the saturation vapor density in the carrier gas.

The disclosed process and device permit measuring the absolute saturation concentration of moisture in fluids such as hydraulic oil. The parameter determination in question in turn permits formulation of a statement regarding the quality of the oil.

DE 101 52 777 A1 discloses a device for determination of the quality of a medium, a lubricant and/or cutting oil in particular, having several sensors generating an electric output signal as a function of the respective sensor-specific input quantity. One sensor is a temperature sensor generating an output signal which is a function in essence exclusively of the temperature of the medium and is essentially independent of the quality of the medium. At least one other sensor generates an output signal as a function both of the quality of the medium (fluid) and of the temperature of the medium. These sensors are mounted on a common substrate immersible in the fluid, so that the measuring device is mounted in a very small structural space.

The disclosed measuring devices and processes indicated in the foregoing make available a very good set of instruments for determination of quality parameters for fluids, including media in the form of a gas and/or paste. Those measuring devices may also be supplemented by chemical analysis processes, for example, in order to arrive at determinations regarding free radicals in a hydraulic oil, temperature, viscosity, pH value, electric conductivity, etc. Such devices entail a prolonged measurement or determination period depending on the measuring process employed, along with the associated measurement device and depending on the quality parameters of the fluid to be determined. Out of consideration of reasons of process accuracy, length of the measurement period, and validity of the test result, it has been found to be advisable to use such quality measurement processes directly on test stands where the operation of fluid devices such as hydraulic assemblies, valves, filter housings, flexible pressure tubing, etc., may be tested. Use of the operating fluid is necessary, on location, to verify the quality of the fluid used by the measuring device, if possible simultaneously with testing of the assembly. In this way, determination is made of the suitability of the fluid device for subsequent operation, in turn, to obtain a broader indication of the quality of the preceding production steps with respect to the fluid device (assembly) which has been or is to be tested.

SUMMARY OF THE INVENTION

An object of the present invention is to provide a device meeting the above requirements.

The object is basically attained by a device for testing at least one quality parameter of a fluid of fluid devices characterized in that at least occasionally a specified volume of fluid is received into at least one fluid space of a particular fluid device and, after leaving the fluid device, may be stored in a storage device by a control device in order subsequently to be fed further to a measuring device for determination of the respective quality parameter of the fluid to be determined.

If a fluid device has been produced, for example, in the form of working cylinders, hydraulic accumulators, valves, filter housings, flexible pressure tubing, etc., and is placed on a testing stand, the functional testing generally has been preceded by a plurality of production steps involving machining to some extent, something which usually results in fouling of the fluid spaces of the respective fluid device. Fouling occurs even if no machining has been carried out, either in the form of dust or in the form of operating media such as corrosion protection means, lubricants, other hydraulic media, etc. If delivery is then made to customers, after appropriate functional testing, in which the operating fluid is admitted to the respective fluid device, fouling matter remaining in the fluid spaces could impede subsequent operation and result both in failure of the respective fluid device and failure of all-hydraulic unit, even if such units are additionally protected by filter devices or the like.

It has been found in practical applications that this danger may be reduced if on the test stand the fluid medium is applied to the fluid spaces of the fluid device involved several times in a sort of scavenging process. The spaces are then emptied of the fluid medium to obtain a yield at least of fouling particles. However, even if a very high number of scavenging processes are carried out, the possibility cannot be excluded that in a special case fouling material may remain in the fluid space and then result in the adverse effects indicated in the hydraulic circuit in subsequent operation of the fluid device. To prevent such occurrence according to the present invention, after the scavenging cycle has been completed, the last amount of fluid introduced is subjected to thorough testing by the appropriate measuring device. If the fluid space is small because of the geometric dimensions of the respective fluid device, the volume of fluid involved may be taken directly to the measurement device for online measurement if the amount of fluid present in the fluid space is sufficient for such online measurement. Otherwise, the amount of fluid required for reliable online measurement may be collected and made available by the device of the present invention. With fluid devices of large dimensions in particular, however, the fluid volumes of the fluid spaces are also large, so that with the online measurement process as outlined a very lengthy measurement period elapses before the entire volume of fluid is tested. The test stand then continues to be occupied and may not be used for testing of another fluid device to be introduced into the test stand. The present invention is introduced at this point, and takes from the large amount of fluid the amount required for online measurement. The device of the present invention is especially well suited for applications in which only brief testing or measurement periods are available. The measurement stand itself accordingly assumes very high measurement cycles and amounts of fluid which depart from the optimum measurement volume, for example, because the amounts of fluid employed are very small or very large.

The device of the present invention now makes it possible for the amount of fluid of the last scavenging cycle to be introduced by a control device into a storage device and from the storage device the fluid to be tested may be moved on to the measuring device. The control device simultaneously permits change of the fluid device to be tested on the test stand. Replacement of the fluid device may accordingly be undertaken while the measurement (testing) proper for the preceding fluid device is still in progress. Hence, the device of the present invention is especially well suited for quality parameter checking in fluid devices if large volumes of fluid are to be tested and/or only brief measurement periods are available for this or other reasons. Because of the intelligent configuration of the control device, preferably as microprocessor equipment, it is possible to use fluid devices having fluid spaces of small dimensions to conduct online testing or testing after a prescribed delay period. Also, it is possible to use the measurement period in question to effect the desired replacement on the test stand. The device of the present invention accordingly helps in lowering the expenditure of time and costs and, because of the solution applied, may be suitably employed in a multiplicity of embodiments.

By preference, the storage device includes a working cylinder, in particular one in the form of a pneumatic cylinder which may be connected on the piston side by a feed line so as to conduct fluid to the associated fluid space of the fluid device by the control device. The measurement device is mounted in the direction of flow of the fluid beyond the working cylinder in a discharge line. If the volume of the storage unit is sufficiently large, if desired several quantities of fluid may be stored for several consecutive rinse cycles and then recalled for the overall measurement. This arrangement permits a statistically improved, firmly established, evaluation and accordingly overall state regarding the quality of the fluid device produced.

The device of the present invention may be used in particular to obtain a reliable indication of the fouling status of the fluid to be tested and thus of the fluid device. Should such be desired, in addition to determination of the number of (fouling) particles, depending on the measurement device employed indications may also be obtained of the size, type, and speed of the particles present in the fluid to be tested. The respective quality parameter test may be further supplemented by other values such as viscosity, temperature, free radicals, pH values, electric conductivity of the fluid to be tested, etc.

Other objects, advantages and salient features of the present invention will become apparent from the following detailed description, which, taken in conjunction with the annexed drawings, discloses a preferred embodiment of the present invention.

BRIEF DESCRIPTION OF THE DRAWINGS

Referring to the drawing which forms a part of this disclosure which is not drawn to scale.

DETAILED DESCRIPTION OF THE INVENTION

Figure 1:
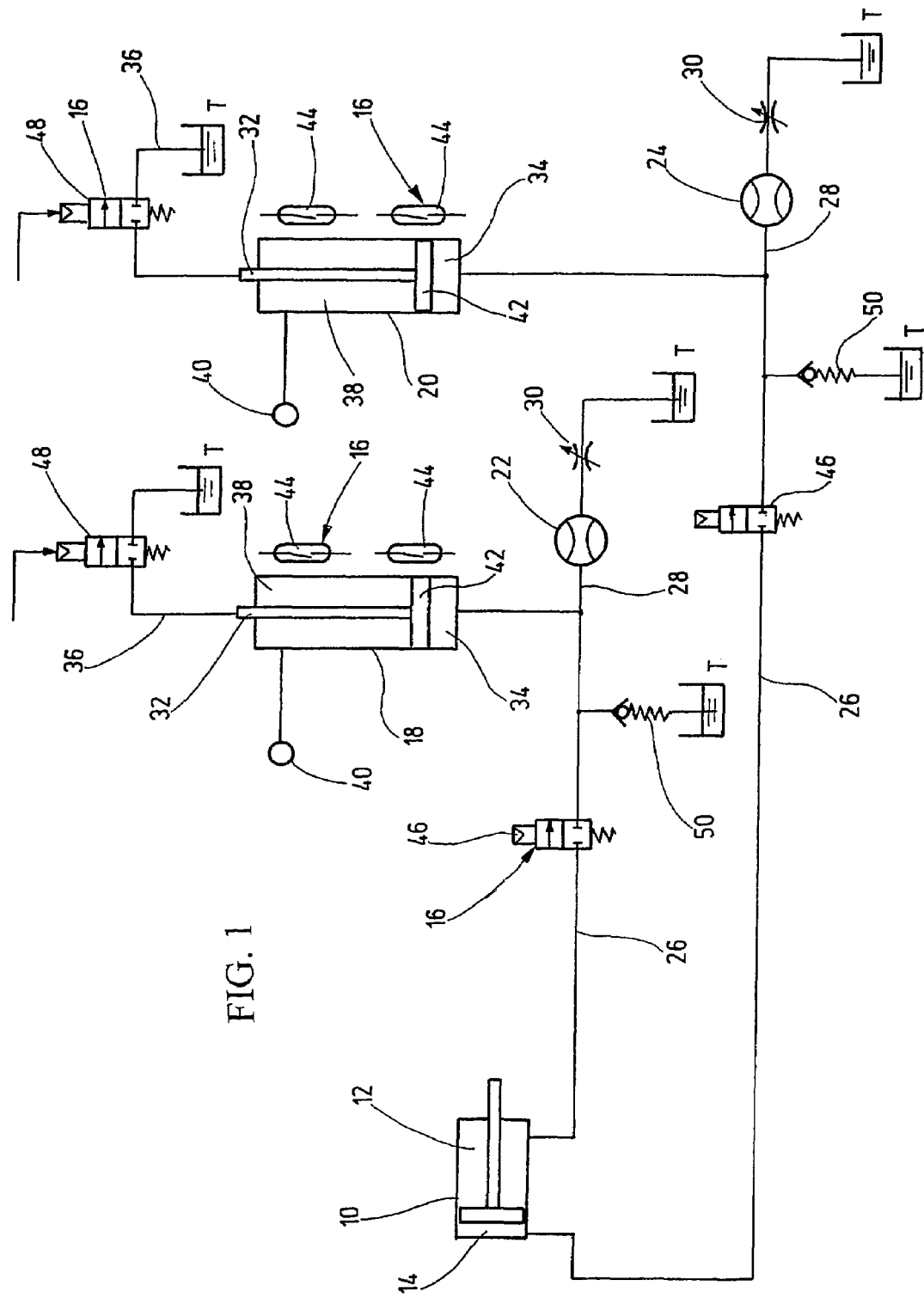
FIG. 1 is a schematic diagram of a device according to an exemplary embodiment of the present invention for testing a hydraulic working cylinder after completion of a specifiable number of testing and scavenging cycles, the hydraulic device carrying out the scavenging cycle being omitted for the sake of greater simplicity of presentation.

The device shown as a whole in FIG. 1 serves the purpose of testing at least one quality parameter of a fluid in fluid devices, such as one in the form of a hydraulic working cylinder 10. That fluid device at least occasionally receives a specified volume of fluid in at least one fluid space. In the present situation, the hydraulic working cylinder 10 has a fluid space 12 on the rod side and a fluid space 14 on the piston side. The respective volume of fluid, after leaving the fluid device, in this instance in the form of the hydraulic working cylinder 10, may be stored by a control device 16 in a storage device. Associated with the fluid space 12 is a first storage device 18. The fluid space 14 on the piston side is associated with another or second storage device 20, which is essentially the same in design as the first storage device 18. The volume of fluid may be moved from the storage device 18, 20 to an associated measurement device 22, 24 to determine the respective quality parameter of the fluid. The measurement devices are essentially equivalent to each other.

A measurement device 22, 24 such as is described in DE 102 47 353 may be employed as the respective measurement device 22, 24. The measurement device as described carries out a process for reducing the dependence of the respective measurement devices on flow for determination of impurities, especially fouling by solids such as particles in fluids, by a particle count sensor. Especially, the particle count sensor operates on the light-blocking principle, and is mounted in a measuring cell of the measurement device having a specified inlet cross-section for the flow of fluid. The sensor generates a light beam cross-sectional area over which the flow of fluid is conducted for detection of the impurity in the flow of fluid. The light beam cross-sectional area selected for the direction of flow of the fluid is greater than such area transverse to the point of entry of the impurity into the light beam cross-sectional area.

The light beam cross-sectional area, preferably generated by a conventional laser, of the particle count sensor then does not illuminate the complete cross-sectional area of the measuring cell, but is distinctly of greater extent in the direction of flow. As a result, even markedly small (fouling) particles, such as ones of a size of 2 µm, can be immediately detected without increase in the cost of measurement with the equipment mounted downstream. An evaluation process suitable for such a particle counter is described in detail in DE 197 35 066 C1, and thus, will not be described in greater length. However, the device disclosed makes it possible reliably to detect even the smallest particle. The possibility also exists of detecting air bubbles in the flow of fluid to arrive at permissible statements concerning the quality of the fluid which may also result from different particle geometries.

Each storage device 16, 18 comprises a working cylinder, in particular one in the form of a pneumatic cylinder of conventional design, connected on the piston side by a feed line 26 to conduct fluid to the fluid space 12, 14 of the fluid device associated with it by the control device 16. The respective measurement device 22, 24 is mounted in the direction of flow of the fluid downstream from the pneumatic working cylinder in a discharge line 28. This discharge line 28 extends from the measurement device 22, 24 through an adjustable choke 30 to the tank side T of the device.

The working cylinder of each of the two storage devices 18, 20 has a piston rod 32 with a through fluid duct (not shown) discharging on one side into the respective piston space 34 of the working cylinder and on its other side into a connecting line 36, which in turn may be blocked by the control device 16. An extension of the connecting line 36 discharges on the tank side T. The rod side 38 of the respective working cylinder is connected to a compressed gas source 40, in particular one in the form of a compressed air or nitrogen source. This source provides an operating pressure of several bar, such as 6 bar. In addition, the movement of displacement of the piston 42 is monitored by a monitoring device 44 as part of the control device 16 with end position switches.

The control device 16 has switching valves, in particular ones in the form of 2/2-way switching valves 46, 48. The switching valves 46, 48 are shown in FIG. 1 in their output blocking position. When in their other switching position, after they have been operated, they clear the path for the fluid. These switching valves 46 and 48 clear or close the fluid conducting path for the feed line 26 and/or the connecting line 36. The control device 16 uses the output signals of the monitoring device 44 in the form of the four end-position switches shown in FIG. 1 to operate the switching valves 46, 48. A pressure control valve 50 is connected to the respective feed line 26 to the pneumatic working cylinder, between the working cylinder and the associated switching valve 46 of the control device 16. This pressure control valve 50 in turn leads to the tank side T.

For the sake of better understanding, the device according to an exemplary embodiment according to the present invention will now be described on the basis of a practical application. The hydraulic working cylinder 10 shown in the FIGURE comes from the factory and undergoes thorough functional testing on a test stand not shown. Since machining processes are also involved in the production of such hydraulic working cylinders, the presence of fouling material in the fluid spaces 12, 14 is expected and may derive from residue of cooling lubricants or the like. Before the device is employed in a practical application the hydraulic working cylinder 10 is scavenged, that is, a fluid is alternately introduced into and removed from the fluid spaces 12, 14. This scavenging serves the purpose of eliminating fouling material from these fluid spaces. Once such scavenging cycle has been completed, first thorough testing is effected by the associated measurement device with the piston in the fluid space 12 retracted on the rod side. For this purpose, the control device 16 opens the switching valve 46 and fluid flows over the feed line 26 into the first storage device 18.

If the switching valve 48 remains closed, the quantity of fluid introduced into the feed line 26 may serve the purpose of scavenging both the valve 46 and the measurement device 22, along with the piston space 34 of the storage device 18. If the switching valve 48 is closed, fluid is forced under pressure into the piston space 34. The piston 42 then rises to an upper end position which is checked or indicated by the monitoring device 44. The fluid now present in the piston space 34 is then to be delivered to the associated measurement device 22 for the examination for the presence of particles already described. If, surprisingly, high pressures occur, the proper state of the system is secured by the pressure control valve 50, which to this extent performs a safety function. The control device 16 now closes the switching valve 46 and, as a result of actuation of the compressed gas source 40, pressurized gas reaches the rod side of the pneumatic cylinder 18 causing the piston 42 to move downward as viewed in FIG. 1. The lower end position of piston 42 is monitored or indicated by the associated end position switch of the monitoring device 44.

The fluid displaced by the piston 42 then moves into the measurement device 22 by the drain line 28 for the particle count indicated and thence to the tank side T via the adjustable choke 30. The measurement cycle proceeds in a similar manner as soon as the amount of fluid in the piston fluid space 14 has been displaced in the direction of the other storage device 20 by return of the piston of the hydraulic working cylinder 10. If the two switching valves 46 are then in their blocking position illustrated in FIG. 1, during the particle measurement itself by the measurement devices 22, 24 the working cylinder 10 which has been present in the test stand up to this point is replaced by a new one. The measurement result for the preceding working cylinder tested by the measurement devices 22, 24 also is present on completion of the replacement. In this way the testing cycle, along with the testing device, is not harmed and very reliable test results are obtained in this instance by the device indicated.

Nor is it necessary to test each working cylinder. Hence, for example, only some of the working cylinders deriving from a processing series need be tested, by conducting statistical evaluation processes. The measuring device used for the purpose is suitable in particular for fluid devices, such as large hydraulic working cylinders 10 having fluid spaces 12, 14 with large volumes. As a rule, the possibility also exists of introducing several scavenging amounts in succession into the respective storage devices, as a function of the size of the hydraulic working cylinder 10, and then later of determining their quality by measurement. Consequently, the device of the present invention is especially well suited for large volume flows and for measurement periods available only for a short time.

If the hydraulic device is of small dimensions, and the fluid spaces 12, 14 of a hydraulic working cylinder 10, for example, are of low volume, the storage device 18, 20 is also of assistance. Measurement with the measurement device 22, 24 may then be effected online during a process of introduction and removal of a cylinder. In this instance, the respective switching valve 46 in the feed lines 26 is to be actuated. In the respective online measurement process with low volumes of fluid, the piston 42 of the respective storage device 18, 20 moves to its respective associated position, and may be suitably effected by the control device.

The device of the present invention need not be restricted to hydraulic working cylinders. As a rule, it is suitable for use with fluid devices of any form into which a specifiable quantity or volume of fluid is introduced periodically. Consequently, applications for hydraulic accumulators, hydraulic valves, flexible pressure tubing, etc., are also conceivable. Nor need measurement be restricted to particle evaluation. Depending on the particular measurement device employed, other data may be obtained, such as free radicals in oil, pH values, electric conductivity, consistency, viscosity, etc.

While one embodiment has been chosen to illustrate the present invention, it will be understood by those skilled in the art that various changes and modifications can be made therein without departing from the scope of the present invention as defined in the appended claims.

What is claimed is:

1. A device for testing at least one quality parameter of a fluid in a fluid device at least periodically receiving a specified volume of fluid into at least one fluid space, comprising:

a storage device receiving and storing a volume of the fluid from the fluid device, and being a working cylinder having a piston side connected to the fluid space by a feed line and having a piston movable therein;

a control device being in fluid communication with said storage device via said feed line controlling flow of the fluid from the fluid device to said storage device;

a measurement device being in fluid communication with and downstream of said storage device via a drain line and being capable of determining a quality parameter of the fluid;

an actuating device connected to a rod side of said working cylinder for moving said piston in said working cylinder; and a monitoring device operatively coupled to and indicating positions of said piston in said cylinder.

2. A device according to claim 1 wherein
said monitoring device indicates end positions of said piston in said working cylinder.

3. A device according to claim 1 wherein
said actuating device comprises a source of compressed gas.

4. A device according to claim 3 wherein
said source comprises a compressed air nitrogen source.

5. A device according to claim 1 wherein
said actuator comprises one of the group consisting of an electrically and/or hydraulically operated supply source and a compressed gas source.

6. A device according to claim 1 wherein
said working cylinder comprises a pneumatic cylinder.

7. A device according to claim 1 wherein
the fluid device comprises one of the group consisting of working cylinders, hydraulic accumulators, valves, filter housings and flexible pressure tubing.

8. A device according to claim 1 wherein
said working cylinder comprises a piston rod with a through fluid conducting passage discharging on one side into a piston space of said working cylinder and on another side into a connecting line blocked by said control device.

9. A device according to claim 8 wherein
said control device comprises switching valves located in and clearing and blocking said feed line and said connecting line; and
said control device is connected to said monitoring device to receive output signals from said monitoring device to actuate said switch valves in response to said output signals.

10. A device according to claim 9 wherein
a pressure control valve is connected to said feed line between said working cylinder and the respective switching valve of said control device.

11. A device according to claim 1 wherein
a second storage device and a second measurement device are in fluid communication with a second fluid space of the fluid device.

12. A device according to claim 1 wherein
said measurement device determines at least one of particle size, particle number, particle speed and particle type present in the fluid, and of viscosity, aging, temperature, pH value and electric conductivity of the fluid.

13. A device according to claim 12 wherein
the fluid device is a first hydraulic cylinder having a piston side and a rod side connectable to said working cylinder and said measurement device, said working cylinder being a pneumatic working cylinder; and
said control device permits replacement of the hydraulic cylinder with a new hydraulic cylinder to be tested while said measurement device determines fluid quality in one of said sides of the first hydraulic cylinder.

14. A device according to claim 11 wherein
the fluid device is a first hydraulic cylinder having a piston side and a rod side forming the fluid spaces, respectively; and
said control device permits replacement of the first hydraulic cylinder with a new cylinder to be tested while said measurement device determines fluid quality in the first hydraulic cylinder.

15. A device according to claim 1 wherein
each said storage device comprises working cylinder having a piston rod with a through fluid conducting passage discharging on one side into a piston space of the respective working cylinder and on another side into a connecting line blocked by said control device.

16. A device according to claim 15 wherein
said control device comprises switching valves located in and clearing and blocking said feed lines and connecting lines; and
said control device is connected to monitoring devices operatively coupled to said storage devices to receive output signals from said monitoring devices to actuate said switch valves in response to said output signals.

17. A device according to claim 16 wherein
a pressure control valve is connected to each said feed line between the respective storage device and the respective switching valve of said control device.

18. A device for testing at least one quality parameter of a fluid in a fluid device at least periodically receiving a specified volume of fluid into at least one fluid space, comprising:
first and second storage devices receiving and storing volumes of the fluid from the fluid device via feed lines;
a control device in fluid communication with said storage devices controlling flow of the fluid from the fluid device to said storage devices; and
first and second measurement devices in fluid communication via discharge lines with and downstream of said first and second storage devices, respectively, capable of determining a quality parameter of the fluid.

19. A device according to claim 18 wherein
each said storage device has a monitoring device operatively coupled thereto indicating end positions of a piston movable within each said storage device.

20. A device according to claim 18 wherein
an actuator comprising one of the group consisting of an electrically and/or hydraulically operated supply source and a compressed gas source is connected to a rod side of each said storage device.

21. A device according to claim 18 wherein
each said storage device comprises a pneumatic cylinder.

22. A device according to claim 18 wherein
the fluid device comprises one of the group consisting of working cylinders, hydraulic accumulators, valves, filter housings and flexible pressure tubing.

23. A device according to claim 18 wherein
said measurement devices determine at least one of particle size, particle number, particle speed and particle type present in the fluid, and of viscosity, aging, temperature, pH value and electric conductivity of the fluid.

24. A device according to claim 23 wherein
the fluid device is a first hydraulic cylinder having a piston side and a rod side connectable to said storage devices and said measurement devices, said storage devices being pneumatic working cylinders; and said control device permits replacement of the first hydraulic cylinder with a new hydraulic cylinder to be tested while said measurement devices determine fluid quality in said sides of the first hydraulic cylinder.

25. A device for testing at least one quality parameter of a fluid in a fluid device at least periodically receiving a specified volume of fluid into at least one fluid space, comprising:

a storage device receiving and storing a volume of the fluid from the fluid device via a feed line;

a control device in said feed line in fluid communication with said storage device controlling flow of the fluid from the fluid device to said storage device; and a measurement device in fluid communication via a discharge line with and downstream of said storage device capable of determining a quality parameter of the fluid, said quality parameter being at least one of particle size, particle number, particle speed and particle type in the fluid, and of viscosity, aging, temperature, pH value and electric conductivity of the fluid.

26. A device according to claim 25 wherein
a monitoring device operatively coupled to storage device indicates end positions of a piston movably mounted in said storage device.

27. A device according to claim 25 wherein
an actuator comprising one of the group consisting of an electrically and/or hydraulically operated supply source and a compressed gas source is connected to a rod side of said storage device.

28. A device according to claim 25 wherein
said storage device comprises a pneumatic cylinder.

29. A device according to claim 25 wherein
said storage device comprises a working cylinder having a piston rod with a through fluid conducting passage discharging on one side into a piston space of said working cylinder and on another side into a connecting line blocked by said control device.

30. A device according to claim 29 wherein
said control device comprises switching valves located in and clearing and blocking said feed line and said connecting line; and said control device is connected to a monitoring device operatively coupled to said storage device to receive output signals from said monitoring device and to actuate said switch valves in response to said output signals.

31. A device according to claim 30 wherein
a pressure control valve is connected to said feed line between said working cylinder and the respective switching valve of said control device.

32. A device according to claim 25 wherein
a second storage device and a second measurement device are in fluid communication with a second fluid space of the fluid device via another feed line.

33. A device according to claim 25 wherein
the fluid device is a first hydraulic cylinder having a piston side and a rod side connectable to said storage device and said measurement device, said storage device being a pneumatic working cylinder; and said control device permits replacement of the first hydraulic cylinder with a new hydraulic cylinder to be tested while said measurement device determines fluid quality in one of said sides of the first hydraulic cylinder.

* * * * *